(12) United States Patent
Gangakhedkar et al.

(10) Patent No.: US 12,146,217 B2
(45) Date of Patent: Nov. 19, 2024

(54) PARTICLE COATING METHODS AND APPARATUS

(71) Applicant: Applied Materials, Inc., Santa Clara, CA (US)

(72) Inventors: Kaushal Gangakhedkar, San Jose, CA (US); Jonathan Frankel, Los Gatos, CA (US); Colin C. Neikirk, Mountain View, CA (US); Pravin K. Narwankar, Sunnyvale, CA (US)

(73) Assignee: Applied Materials, Inc., Santa Clara, CA (US)

( * ) Notice: Subject to any disclaimer, the term of this patent is extended or adjusted under 35 U.S.C. 154(b) by 247 days.

(21) Appl. No.: 17/590,614

(22) Filed: Feb. 1, 2022

(65) Prior Publication Data

US 2022/0186372 A1    Jun. 16, 2022

Related U.S. Application Data

(62) Division of application No. 16/515,875, filed on Jul. 18, 2019, now Pat. No. 11,242,599.

(60) Provisional application No. 62/700,753, filed on Jul. 19, 2018.

(51) Int. Cl.
    C23C 16/44      (2006.01)
    A61K 9/16       (2006.01)
    C23C 16/455     (2006.01)
(52) U.S. Cl.
    CPC ...... *C23C 16/45544* (2013.01); *A61K 9/1611* (2013.01); *A61K 9/1629* (2013.01); *C23C 16/4408* (2013.01); *C23C 16/4417* (2013.01)

(58) Field of Classification Search
    None
    See application file for complete search history.

(56) References Cited

U.S. PATENT DOCUMENTS

| 3,818,982 A | 6/1974 | Wagner |
| 4,606,941 A | 8/1986 | Jenkin |
| 6,613,383 B1 | 9/2003 | George et al. |

(Continued)

FOREIGN PATENT DOCUMENTS

| CN | 105392918 | 3/2016 |
| CN | 107365974 | 11/2017 |

(Continued)

OTHER PUBLICATIONS

Office Action in Chinese Appln. No. 201980052781.X, dated Aug. 15, 2022, 17 pages (with English translation).

(Continued)

*Primary Examiner* — Shamim Ahmed
*Assistant Examiner* — Bradford M Gates
(74) *Attorney, Agent, or Firm* — Fish & Richardson P.C.

(57) ABSTRACT

A reactor for coating particles includes a vacuum chamber configured to hold particles to be coated, a vacuum port to exhaust gas from the vacuum chamber via the outlet of the vacuum chamber, a chemical delivery system configured to flow a process gas into the particles via a gas inlet on the vacuum chamber, one or more vibrational actuators located on a first mounting surface of the vacuum chamber, and a controller configured to cause the one or more vibrational actuators to generate a vibrational motion in the vacuum chamber sufficient to induce a vibrational motion in the particles held within the vacuum chamber.

13 Claims, 2 Drawing Sheets

(56) References Cited

U.S. PATENT DOCUMENTS

| | | |
|---|---|---|
| 11,242,599 B2 | 2/2022 | Gangakhedkar et al. |
| 2011/0116984 A1 | 5/2011 | Rehmat et al. |
| 2011/0200822 A1 | 8/2011 | Detavernier et al. |
| 2012/0085284 A1 | 4/2012 | Dassel |
| 2013/0059073 A1 | 3/2013 | Jiang et al. |
| 2014/0127756 A1 | 5/2014 | Bolz et al. |
| 2015/0125599 A1 | 5/2015 | Lindfors et al. |
| 2016/0083837 A1 | 3/2016 | Narushima |
| 2016/0258059 A1 | 9/2016 | Lee et al. |
| 2017/0327948 A1 | 11/2017 | Dadheech et al. |
| 2018/0221294 A1 | 8/2018 | Carlsson et al. |
| 2019/0249302 A1 | 8/2019 | Pudas |

FOREIGN PATENT DOCUMENTS

| | | |
|---|---|---|
| EP | 2948573 | 10/2017 |
| JP | H02-30766 | 2/1990 |
| JP | 2010-209419 | 9/2010 |
| JP | 2015-520297 | 7/2015 |
| JP | 2016-508544 | 3/2016 |
| KR | 10-2011-0119871 | 11/2011 |
| KR | 10-2015-0013296 | 2/2015 |
| WO | WO 2007/123510 | 11/2007 |
| WO | WO 2014/044907 | 3/2014 |
| WO | WO 2014/114844 | 7/2014 |
| WO | WO 2014/178160 | 11/2014 |
| WO | WO 2017/108636 | 6/2017 |
| WO | WO 2018/050954 | 3/2018 |

OTHER PUBLICATIONS

International Search Report and Written Opinion in International Appln. No. PCT/US2019/042333, dated Oct. 25, 2019, 12 pages.

Office Action in Indian Appln. No. 202147005834, dated Mar. 24, 2021, 6 pages.

Office Action in Japanese Appln. No. 2021-501314, dated Apr. 5, 2022, 8 pages (with English translation).

Supplemental Search Report in European Appln. No. 19838650.0, dated Mar. 25, 2022, 7 pages.

PARTICLE COATING METHODS AND APPARATUS

CROSS-REFERENCE TO RELATED APPLICATIONS

This application is a divisional application and claims priority to U.S. patent application Ser. No. 16/515,875, filed on Jul. 18, 2019, which claims priority to U.S. Provisional Patent Application Ser. No. 62/700,753, filed on Jul. 19, 2018, the disclosures of which are incorporated by reference.

TECHNICAL FIELD

This disclosure pertains to coating particles, e.g., particles that include active pharmaceutical ingredients, with thin organic and inorganic films.

BACKGROUND

It is of great interest to the pharmaceutical industry to develop improved formulations of active pharmaceutical ingredients (API). Formulation can influence the stability and bioavailability of the API as well as other characteristics. Formulation can also influence various aspects of drug product (DP) manufacture, for example, ease and safety of the manufacturing process.

Numerous techniques for encapsulating or coating API have been developed. Some existing techniques for the coating of API include spray coating, plasma polymerization, and hot wire chemical vapor deposition (CVD). Spray coating is an industrially scalable technique that has been widely adopted by the pharmaceutical industry. However, coating non-uniformities (both within a particle and from particle to particle) prevent the use of these techniques for improving the delivery profile or stability of active pharmaceutical ingredients (APIs). Particle agglomeration during spray coating also causes significant challenges. Meanwhile, techniques such as plasma polymerization are difficult to scale, applicable only to certain precursor chemistries, and can result in the degradation of sensitive APIs. Hot wire systems have been developed that utilize a cold substrate as the condensation media for gases and radicals. Rotary reactors include atomic layer deposition (ALD) and initiated CVD (iCVD) reactors. However, ALD reactors are suitable for inorganic coatings and not for organic polymer coatings, and existing iCVD designs do not adequately prevent API degradation and are not scalable for high volume manufacturing. Other techniques include polymer mesh coating, pan coating, aerosolized coating, and fluidized bed reactor coating.

SUMMARY

In general, one innovative aspect of the subject matter described in this specification can be embodied in a method for coating particles that includes dispensing particles into a processing volume of a vacuum chamber, where the processing volume is defined by one or more sidewalls of the vacuum chamber, a first filter, and a second filter, evacuating the processing volume through a vacuum port on the vacuum chamber, agitating particles disposed in the processing volume of the vacuum chamber by vibrating the vacuum chamber at a frequency between 30 Hz and 300 Hz, flowing a first precursor into the processing volume through a gas inlet on the vacuum chamber and through the second filter and reacting the particle surfaces of the particles with the first precursor as the particles are agitated to form a first layer, and flowing a second precursor into the processing volume via the gas inlet and reacting the first layer with the second precursor as the particles are agitated to form a thin film.

Implementations may include one or more of the following features. In some implementations, dispensing particles into the processing volume of the vacuum chamber further includes placing a porous processing vessel enclosing the particles into the processing volume, where the porous processing vessel includes the first filter and the second filter.

In some implementations, the particles have a dimension less than about 300 micron.

In some implementations, the second precursor includes a moiety of arsenic, boron, carbon, fluorine, hydrogen, nitrogen, oxygen, phosphorus, selenium, sulfur, tellurium, an alkyl group, an aryl group, or combinations thereof. The thin film coating can include a carbide, fluoride, nitride, oxide, phosphide, sulfide, or alloy composition of one or more of Al, B, Ba, Ca, Co, Cu, Fe, Ga, Ge, Hf, In, La, Mg, Nb, Ni, Pt, Ru, Sb, Si, Sr, Ta, Ti, V, W, Y, Zn, and Zr.

In some implementations, the first precursor includes a moiety of Al, Ag, B, Ba, Be, Bi, Ca, Cd, Ce, Co, Cr, Cu, Dy, Eu, Er, Fe, Ga, Gd, Ge, Hf, Hg, Ho, In, Ir, La, Li, Lu, Mo, Mg, Mn, Nb, Nd, Ni, Os, Pd, Pr, Pt, Ru, Sb, Sc, Si, Sm, Sn, Sr, Ta, Ti, Tm, V, W, Y, Yb, Zn, Zr, or combinations thereof. The first precursor can further include a moiety of an alkyl group, an alkoxide group, an alkylamide group, an amidinate group, a carbonyl group, a cyclopentadienyl group, a β-diketonate group, a guandinate group, a halogen, or combinations thereof.

The method can further include flowing a purge gas into the processing volume between flowing the first precursor and flowing the second precursor. In some implementations, the method includes multiple repeated cycles of flowing the first precursor into the processing volume, flowing the purge gas into the processing volume, and flowing the second precursor into the processing volume.

In some implementations, the vacuum chamber is located on and supported by a vibrational table. The methods can include coating the particles by atomic layer deposition or molecular layer deposition.

In general, another innovative aspect of the subject matter described in this specification can be embodied in a reactor for coating particles including vacuum chamber configured to hold particles to be coated, a vacuum port to exhaust gas from the vacuum chamber via the outlet of the vacuum chamber, a chemical delivery system configured to flow a process gas into the particles via a gas inlet on the vacuum chamber, a table to support the vacuum chamber on a first mounting surface of the table, a base and one or more resilient members located between the table and the base and supportive of the table onto a second mounting surface opposite the first mounting surface, one or more vibrational actuators located between the table and the base, and a controller configured to cause the one or more vibrational actuators to generate a vibrational motion in the table sufficient to induce a vibrational motion in the particles held within the vacuum chamber.

These and other embodiments may include one or more of the following features. In some implementations, the vacuum chamber further includes a lid, a bottom, one or more sidewalls, a first filter, disposed between the lid and the bottom, and a second filter, disposed between the first filter and the bottom. The first filter, the second filter, and the one or more sidewalls can define a first volume.

In some implementations, the reactor further includes a porous processing vessel holding the particles, wherein the porous processing vessel is located within the first volume. The porous processing vessel can include the first filter and the second filter.

In some implementations, the second filter is spaced from the bottom to define a second volume between the second filter, the bottom, and the one or more sidewalls, and/or the first filter is spaced from the lid to define a third volume between the first filter, the lid, and the one or more sidewalls.

In some implementations, the vacuum port on the vacuum chamber is located on the vacuum chamber such that process gas is exhausted from the first volume through the third volume. The gas inlet on the vacuum chamber can be located on the vacuum chamber such that process gas flows into the first volume via the second volume.

In some implementations, the chemical delivery system includes a first precursor gas and a second precursor gas. The controller can be configured to cause the one or more vibrational actuators to induce a vibrational frequency between 30 Hz and 300 Hz.

In general, another innovative aspect of the subject matter described in this specification can be embodied in a reactor for coating particles including a vacuum chamber configured to hold particles to be coated, a vacuum port to exhaust gas from the vacuum chamber via the outlet of the vacuum chamber, a chemical delivery system configured to flow a process gas into the particles via a gas inlet on the vacuum chamber, one or more vibrational actuators located on a first mounting surface of the vacuum chamber, and a controller configured to cause the one or more vibrational actuators to generate a vibrational motion in the vacuum chamber sufficient to induce a vibrational motion in the particles held within the vacuum chamber.

Implementations may include, but are not limited to, one or more of the following possible advantages. Particles, e.g., API particles, can be coated within a high volume manufacturing process, thereby providing lower cost of manufacturing and reduced drug product prices. Particles can be coated with thin layer(s), thus providing a drug product with an advantageous volume fraction of API. In addition, the process can result in layer(s) encapsulating the API that are uniform within a particle and from particle-to-particle, providing more consistent properties to the drug formulations. The process can utilize high shear agitation that can break down aggregates more effectively, improving the uniformity of mixing of gas and particles and resulting in a uniform coating. The process can be performed without internal agitation, e.g., paddle mixing, simplifying the wetted hardware involved and making the system easier to clean and potentially easier to scale.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting.

Other features and advantages of the invention will be apparent from the following detailed description and figures, and from the claims.

BRIEF DESCRIPTION OF THE DRAWINGS

Like reference numbers and designations in the various drawings indicate like elements.

DETAILED DESCRIPTION

There are various methods for encapsulating API particles. In many cases, these methods result in a coating that is relatively thick. While such coatings can impart desirable properties, the high ratio of coating to API can make it difficult to create a drug product in which the volume fraction of API is as high as desired. In addition, the coating encapsulating the API can be non-uniform, making it difficult to provide formulations with consistent properties. Furthermore, coating techniques that can provide satisfactory consistency have not be scalable for industrial manufacturing.

An approach that may address these issues is to use a vibrating reactor chamber. The process gas can be forced through a first filter located below and supportive of the particle bed and exhausted through a second filter located above the particle bed and opposite the first filter such that the process gas percolates through the particle bed. Vibration induced in the particle bed can ensure separation of particles so that the process gas can flow between particles, which can improve uniformity of coating across the particles.

Drug

The term "drug," in its broadest sense includes all small molecule (e.g., non-biologic) APIs. The drug could be selected from the group consisting of an analgesic, an anesthetic, an anti-inflammatory agent, an anthelmintic, an anti-arrhythmic agent, an antiasthma agent, an antibiotic, an anticancer agent, an anticoagulant, an antidepressant, an antidiabetic agent, an antiepileptic, an antihistamine, an antitussive, an antihypertensive agent, an antimuscarinic agent, an antimycobacterial agent, an antineoplastic agent, an antioxidant agent, an antipyretic, an immunosuppressant, an immunostimulant, an antithyroid agent, an antiviral agent, an anxiolytic sedative, a hypnotic, a neuroleptic, an astringent, a bacteriostatic agent, a beta-adrenoceptor blocking agent, a blood product, a blood substitute, a bronchodilator, a buffering agent, a cardiac inotropic agent, a chemotherapeutic, a contrast media, a corticosteroid, a cough suppressant, an expectorant, a mucolytic, a diuretic, a dopaminergic, an antiparkinsonian agent, a free radical scavenging agent, a growth factor, a haemostatic, an immunological agent, a lipid regulating agent, a muscle relaxant, a parasympathomimetic, a parathyroid calcitonin, a biphosphonate, a prostaglandin, a radio-pharmaceutical, a hormone, a sex hormone, an anti-allergic agent, an appetite stimulant, an anoretic, a steroid, a sympathomimetic, a thyroid agent, a vaccine, a vasodilator and a xanthine.

Exemplary types of small molecule drugs include, but are not limited to, acetaminophen, clarithromycin, azithromycin, ibuprofen, fluticasone propionate, salmeterol, pazopanib HCl, palbociclib, and amoxicillin potassium clavulanate.

Pharmaceutically Acceptable Excipients, Diluents, and Carriers

Pharmaceutically acceptable excipients include, but are not limited to:

(1) surfactants and polymers including: polyethylene glycol (PEG), polyvinylpyrrolidone (PVP), sodium lauryl sulfate, polyvinylalcohol, crospovidone, polyvinylpyrrolidone-polyvinylacrylate copolymer, cellulose derivatives, hydroxypropylmethyl cellulose, hydroxypropyl cellulose, carboxymethylethyl cellulose, hydroxypropyllmethyl cellulose phthalate, polyacrylates and polymethacrylates, urea, sugars, polyols, carbomer and their polymers, emulsifiers, sugar gum, starch, organic acids and their salts, vinyl pyrrolidone and vinyl acetate;
(2) binding agents such as cellulose, cross-linked polyvinylpyrrolidone, microcrystalline cellulose;
(3) filling agents such as lactose monohydrate, lactose anhydrous, microcrystalline cellulose and various starches;
(4) lubricating agents such as agents that act on the flowability of a powder to be compressed, including colloidal silicon dioxide, talc, stearic acid, magnesium stearate, calcium stearate, silica gel;
(5) sweeteners such as any natural or artificial sweetener including sucrose, xylitol, sodium saccharin, cyclamate, aspartame, and acesulfame K;
(6) flavoring agents;
(7) preservatives such as potassium sorbate, methylparaben, propylparaben, benzoic acid and its salts, other esters of parahydroxybenzoic acid such as butylparaben, alcohols such as ethyl or benzyl alcohol, phenolic chemicals such as phenol, or quarternary compounds such as benzalkonium chloride;
(8) buffers;
(9) Diluents such as pharmaceutically acceptable inert fillers, such as microcrystalline cellulose, lactose, dibasic calcium phosphate, saccharides, and/or mixtures of any of the foregoing;
(10) wetting agents such as corn starch, potato starch, maize starch, and modified starches, and mixtures thereof;
(11) disintegrants; such as croscarmellose sodium, crospovidone, sodium starch glycolate; and
(12) effervescent agents such as effervescent couples such as an organic acid (e.g., citric, tartaric, malic, fumaric, adipic, succinic, and alginic acids and anhydrides and acid salts), or a carbonate (e.g., sodium carbonate, potassium carbonate, magnesium carbonate, sodium glycine carbonate, L-lysine carbonate, and arginine carbonate) or bicarbonate (e.g. sodium bicarbonate or potassium bicarbonate)

Metal Oxide Material

The term "metal oxide material," in its broadest sense includes all materials formed from the reaction of elements considered metals with oxygen-based oxidants. Exemplary metal oxide materials include, but are not limited to, aluminum oxide, titanium dioxide, iron oxide, gallium oxide, magnesium oxide, zinc oxide, niobium oxide, hafnium oxide, tantalum oxide, lanthanum oxide, and zirconium dioxide. Exemplary oxidants include, but are not limited to, water, ozone, and inorganic peroxide.

Atomic Layer Deposition (ALD)

Atomic layer deposition is a thin film deposition technique in which the sequential addition of self-limiting monolayers of an element or compound allows deposition of a film with thickness and uniformity controlled to the level of an atomic or molecular monolayer. Self-limited means that only a single atomic layer is formed at a time, and a subsequent process step is required to regenerate the surface and allow further deposition.

Molecular Layer Deposition (MLD)

Molecular layer deposition is analogous to atomic layer deposition but using organic precursors and forming organic thin films. During a typical MLD process, two homo-bifunctional precursors are used. A first precursor is introduced into a chamber. The molecules of the first precursor react with reactive groups on the substrate surface via the corresponding linking chemistry to add a molecular layer of the first precursor on the substrate surface with new reactive sites. After purging, a second precursor is introduced and the molecules of the second precursor react with the new reactive sites provided by the first precursor generating a molecular layer of the first precursor linked to the second precursor. This is followed by another purge cycle.

Reactor System

Figure 1:
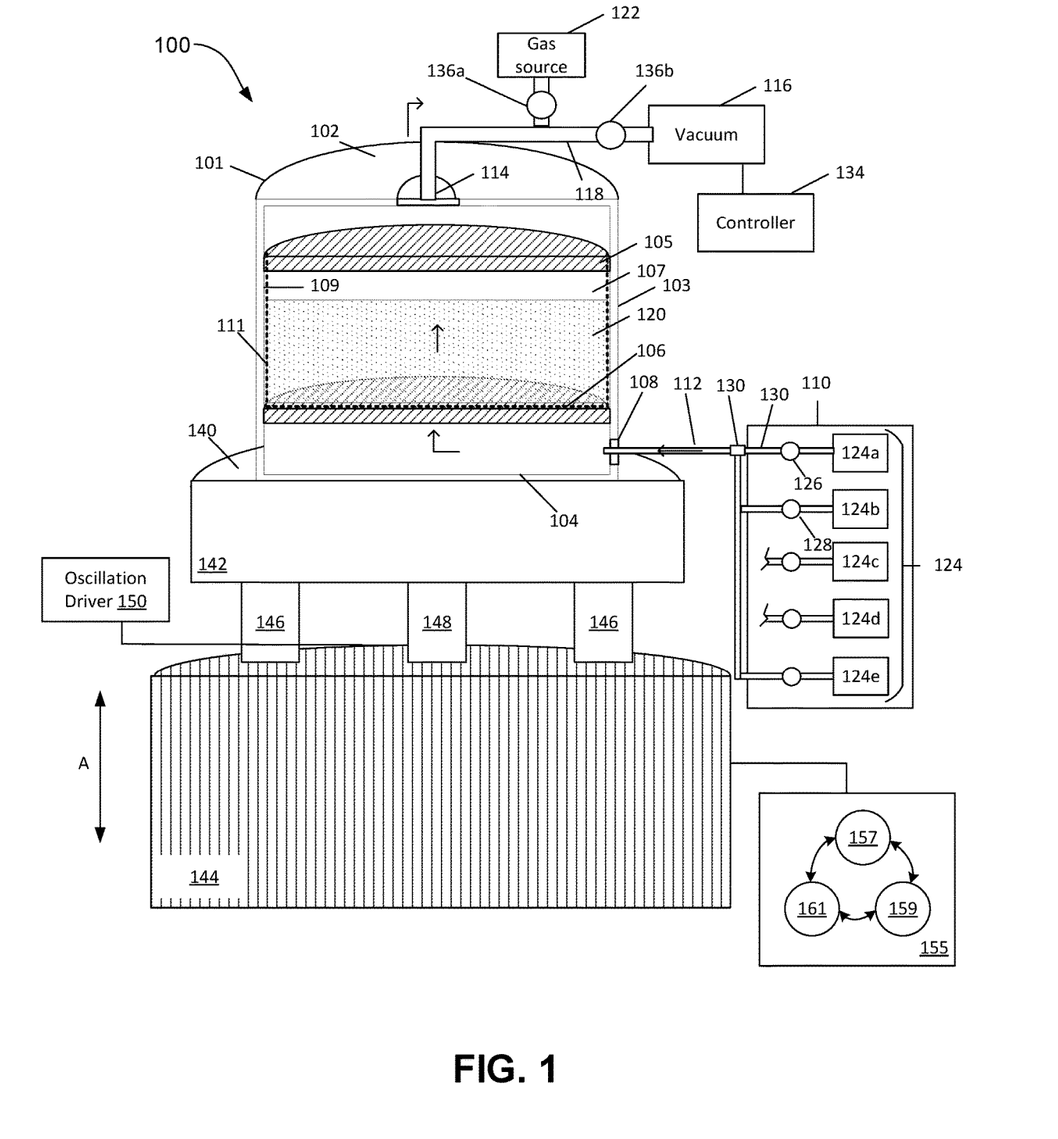
FIG. 1 is a schematic isometric cross-sectional view of an example reactor system for ALD and/or CVD coating of particles, e.g., drugs.

FIG. 1 illustrates a reactor system 100 for coating particles with a thin-film coating. The reactor system 100 can perform the coating using ALD and/or MLD coating conditions. The reactor system 100 permits a deposition process (ALD or MLD), to be performed at higher (above 50° C., e.g., 50-100° C.) or lower processing temperature, e.g., below 50° C., e.g., at or below 35° C. For example, the reactor system 100 can form thin-film metal oxides on the particles primarily by ALD at temperatures of 22-35° C., e.g., 25-35° C., 25-30° C., or 30-35° C. In general, the particles can remain or be maintained at such temperatures. This can be achieved by having the reactant gases and/or the interior surfaces of the reactor chamber remain or be maintained at such temperatures. For example, heating can be achieved by a heater cartridge embedded in chamber body, by water channel in chamber body with use of heat exchanger, or by a heater jacket on the chamber body.

In some embodiments, the particles are microscale particles where at least one dimension of the particle is less than 100 microns or ranges between 0.1 microns to 100 microns. In some embodiments, the particles are nanoscale particles where at least one dimension of the particles is less than 100 nm, e.g., between 1 nanometer (nm) and 100 nm. In some embodiments, the particles are of a size that such at least one dimension of the particle is less than about 300 microns.

The reactor system 100 includes a vacuum chamber 101 including a lid 102. The vacuum chamber includes one or more sidewalls 103 and a bottom 104. A first filter 105 located between the lid 102 and the bottom 104, and a second filter 106, located between the first filter and the bottom 104, are enclosed within the vacuum chamber 101. The sidewalls 103, first filter 105, and the second filter 106 collectively define the boundaries of a first volume, e.g., a processing volume 107. The sidewalls 104, bottom 104, and lid 102 of the vacuum chamber 101 can be a material, e.g., stainless steel, that is inert to the deposition process, and/or the interior surfaces of the 109 can be coated with a material that is inert to the deposition process.

One or more process gases are introduced into the processing volume 107 through a gas inlet 108 via one or more of the sidewalls 103, lid 102 or bottom 104 of the vacuum chamber 101. As depicted in FIG. 1, gas inlet 108 is located on a sidewall 103 of the vacuum chamber 101 and coupled to a chemical delivery system 110 located outside the vacuum chamber 101 via a gas delivery manifold 112. The vacuum chamber 101 can include one or more vacuum ports 114 for exhausting gas, e.g., process gas, from the vacuum chamber 101. The vacuum port 114 can be located in the sidewalls 103, lid 102, or bottom 104 of the vacuum chamber 101. As depicted in FIG. 1, the vacuum port 114 is located within the lid 102 of the vacuum chamber 101. In some implementations, the vacuum port 114 is located opposite the processing volume 107 from the inlet 108.

The processing volume 107 is in fluid communication with a vacuum source 116, such as to one or more dedicated vacuum pumps, through vacuum port 114 and an exhaust manifold 118. The vacuum source 116 is used to maintain the processing volume 107 at sub-atmospheric conditions and evacuate unreacted processing gas and gaseous reaction byproducts from the vacuum chamber 101. The first filter 105, located between the processing volume 107 and the vacuum port 114, facilitates the evacuation of unreacted processing gas and gaseous reaction byproducts from the processing volume 107 while preventing solid particles 120 from being purged from the volume 107 unintentionally. Here, the vacuum chamber 101 is a batch-processing vessel where solid particles 120 are loaded into and removed from the processing volume 107 by removing the lid 102 and the first filter 105. The loading and unloading of the particles 120 can be performed manually by a human operator or automatically/semi-automatically using a robot-assisted loading/unloading mechanism.

In some implementations, the reactor system 100 includes a porous processing vessel 111 that is configured to hold the particles 120 inside the processing volume 107. The porous processing vessel 111 can be loaded/unloaded into the vacuum chamber 101 by removing or lifting a portion of the lid 102. The porous processing vessel 111 can be, for example, a bag or other container of an inert chemical composition, e.g., plastic, aluminum, etc., where flow of gas is possible via holes in the porous processing vessel 111 while retaining the particles 120 within the vessel 111. The porous processing vessel 111 can be, for example, a bag formed of a flexible film, e.g., a plastic bag. The holes or pores in the porous processing vessel 111 are configured to be smaller than the particle size of the particles being processed while still allowing flow of process gas through the porous processing vessel 111.

The porous processing vessel 111 can allow for easy loading/unloading of the particles 120 into the reactor 100 and for processing of the particles 120 while minimizing the contact of the particles with the inside of the vacuum chamber 101, thereby reducing the required cleaning of the reactor 100 between batch processes.

In some implementations, porous processing vessel 111 includes an opening aligned with the lid 102 of the vacuum chamber 101, e.g., where the opening of the vessel 111 can be sealed between the sidewalls 103 of the vacuum chamber 101 and the lid 102 when the lid 102 is placed on the vacuum chamber 101. In some implementations, the first filter 105 and second filter 106 are a part of the porous processing vessel 111, where the processing volume 107 is enclosed within the porous processing vessel 111. The porous processing vessel 111 can replace the second filter 106, where the porous processing vessel 111 is configured to retain the particles 120 while allowing for gas flow from the chemical distribution system 110 via the gas inlet 108 into the processing volume 107.

In some implementations, a gas source 122 is coupled to the gas exhaust manifold 118, e.g., a purge gas to dilute process gas that is exhausted from the system 100. Gas exhaust manifold 118 is configured to establish vacuum within the vacuum chamber 101. The vacuum source 116 can be an industrial vacuum pump sufficient to establish pressures less than 1 Torr, e.g., 1 to 100 mTorr, e.g., 50 mTorr. The vacuum source 116 permits the vacuum chamber 101 to be maintained at a desired pressure, and permits removal of reaction byproducts and unreacted process gases.

The chemical delivery system 110 includes multiple fluid sources 124 coupled by respective delivery tubes 126, controllable valves 128, and a fluid supply line 130. The chemical delivery system 110 delivers fluid to the gas delivery manifold 112 that inject the fluid in a vapor form into the vacuum chamber 101 via the gas inlet port 108. The chemical delivery system 110 can include a combination of restrictors, gas flow controllers, pressure transducers, and thermal mass flow controllers/meters to provide controllable flow rate of the various gasses into the vacuum chamber 101. The chemical delivery system 110 can also include one or more temperature control components, e.g., a heat exchanger, resistive heater, etc., to heat or cool the various gasses before they flow into the chamber 101.

The chemical delivery system 110 can include five fluid sources 124a, 124b, 124c, 124d, and 124e. Two of the fluid sources, e.g., fluid sources 124a, 124b, can provide the two chemically different precursors or reactants for the deposition process for forming a metal oxide layer on the particles. For example, the first fluid source 124a can provide trimethylaluminum (TMA) or titanium tetrachloride (TiCl4), whereas the fluid gas source 124b can provide water. Another two of the fluid sources, e.g., fluid sources 124c, 124d, can provide the two chemically different precursors or reactants for the deposition process for forming a polymer material on the metal oxide layer. For example, the third fluid source 124c can provide adipoyl chloride, and the fourth gas source 124d can provide ethylene diamine. One of the fluid sources, e.g., the fifth fluid source 124e, can provide an inert gas, e.g., argon or $N_2$, for purging between cycles or half-cycles in the deposition process.

Although FIG. 1 illustrates five fluid sources, the use of fewer gas sources could still be compatible with deposition of a metal oxide or polymer layer, and use of more gas sources could enable formation of an even wider variety of laminate structures.

For one or more of the fluid sources, the chemical delivery system 110 delivers the precursor or reactant in liquid form to the gas delivery manifold 112. The chemical delivery system 110 can include a vaporizer 132 to convert the liquid to vapor immediately before the precursor or reactant enters a gas inlet 108. This reduces upstream pressure loss to enable more pressure loss to occur across the particles 120 within the chamber 101. The more pressure loss that occurs across the particles 120, the lower the injection apertures can be place, and the more likely that all of the precursor will be reacted as it traverses the particle bed for a given flow rate. The vaporizer 132 can be immediately adjacent the outer wall of the vacuum chamber 101, e.g., secured to or housed adjacent to the gas inlet port 108. As shown in FIG. 1, gas delivery manifold 112 can be utilized to supply multiple precursor or reactant fluid sources 124. Manifold 112 is fluidically connected to gas inlet port 108.

An inert carrier gas, e.g., $N_2$, can flow from one of the fluid sources, e.g., the fluid source 124e, into the chamber 101. In operation, the carrier gas can flow continuously into the vacuum chamber 101, i.e., whether or not the precursor or reactor gas is flowing into the vacuum chamber 101. When the precursor or reactor gas is not being injected into the chamber 101, the flow of the carrier gas can prevent back-streaming into the gas inlet 108 of another precursor or reactor gas. The flow of carrier gas can also prevent fouling of the gas inlet 108, e.g., blockage of the aperture, by the particles 120. In addition, the carrier gas can provide the purge gas for the purge operation when the precursor or reactor gas is not being injected into the chamber 101.

The flow of carrier gas into the vaporizer 132 when the precursor gas is also flowing can improve vaporization of the precursor or reactant liquid. Without being limited by any particular theory, the carrier gas flow can assist in shearing the liquid during aerosolization, which can lead to smaller droplet size, which can be vaporized more quickly. Flow of the carrier gas into the vacuum chamber 101 when the precursor gas is also flowing can assist in drawing precursor gas out of the vaporizer 132.

In some implementations, one or more temperature control components are integrated into the inner chamber walls 109 to permit control of the temperature of the vacuum chamber 101. For example, resistive heater, a thermoelectric cooler, a heat exchanger, or coolant flowing in cooling channels in the chamber wall, or other component in or on the sidewalls 103.

System 100 further includes a controller 134 that is operable to control the actions of at least the chemical distribution system 110. The controller 134 can also be coupled to various sensors, e.g., pressure sensors, flow meters, etc., to provide closed loop control of the pressure of the gasses in the chamber 101.

In general, the controller 134 is configured to operate the reactor system 100 in accord with a "recipe." The recipe specifies an operating value for each controllable element as a function of time. For example, the recipe can specify the times during which the vacuum source 116 is to operate, the times of and flow rate for each gas source 124a-124e, etc. The controller 134 can receive the recipe as computer-readable data (e.g., that is stored on a non-transitory computer readable medium). Methods for operation of the reactor system 100 are described in further detail below.

In some implementations, the system 100 can include a filter cleaner to clear particles off the first filter 105 and second filter 106. As one example, the filter cleaner can be a mechanical knocker to strike the filter; this shake particles off the filter. As another example, gas source 122 can periodically provide a pulse of inert gas, e.g., nitrogen, into the exhaust manifold 118 between the vacuum port 114 and the vacuum source 116. The pulse of gas travels through the first filter 105 into the volume 107 and can blow the particles off the first filter 105. Isolation valves 136a, 136b can be used to ensure that only one of the gas source 122 or vacuum source 116 is fluidically coupled at a time to the exhaust manifold 118.

The reactor system 100 is supported by and affixed securely to a vibration assembly 140. The vibration assembly 140 includes a table 142, base 144, and one or more resilient members 146 mechanically coupling the table 142 to the base 144. Vibration assembly includes one or more vibrational actuators 148 located between and mechanically coupling the table 142 and base 144, and an oscillation driver 150 configured to drive oscillatory motion in the vibrational actuators 148 at a desired vibrational frequency that translates into a vibrational motion of the table 142 along a vibrational axis A at the desired vibrational frequency.

In some implementations, the vibrational frequency is chosen to generate microscale mixing zones to the bulk of the particles 120 within the processing volume 107 based on a resonant frequency of the table 142 that is mechanically coupled to the vacuum chamber 101. In some embodiments, vibrational motion can be induced that is parallel to gravity. In some implementations, the vibrational motion can be induced that is perpendicular to a surface of filters 105, 106. Vibrational motion can be alternated between being parallel to gravity and perpendicular to the surfaces of the filters 105, 106, e.g., alternated during a coating process. The vibrational frequency can be maintained at between 30 Hz and 300 Hz, e.g., between 30-150 Hz during the coating processes described in further detail below.

Typically, operation and control of the system 100 is facilitated using a system controller coupled to the system 100. The system controller 155 includes a programmable central processing unit (CPU) 157 that is operable with a memory 159 (e.g., non-volatile memory) and support circuits 161. The support circuits 161 are conventionally coupled to the CPU 157 and comprise cache, clock circuits, input/output subsystems, power supplies, and the like, and combinations thereof coupled to the various components of the processing system 100, to facilitate control of a thin film deposition process. The CPU 157 is one of any form of general-purpose computer processor used in an industrial setting, such as a programmable logic controller (PLC), for controlling various components and sub-processors of the processing system 100. The memory 159, coupled to the CPU 157, is non-transitory and is typically one or more of readily available memories such as random access memory (RAM), read only memory (ROM), floppy disk drive, hard disk, or any other form of digital storage, local or remote.

Here, the memory 159 is in the form of a computer-readable storage media containing instructions (e.g., non-volatile memory), that when executed by the CPU 157, facilitates the operation of the processing system 100. The instructions in the memory 159 are in the form of a program product such as a program that implements the methods of the present disclosure. The program code may conform to any one of a number of different programming languages. In one example, the disclosure may be implemented as a program product stored on computer-readable storage media for use with a computer system. The program(s) of the program product define functions of the embodiments (including the methods described herein).

Illustrative computer-readable storage media include, but are not limited to: (i) non-writable storage media (e.g., read-only memory devices within a computer such as CD-ROM disks readable by a CD-ROM drive, flash memory, ROM chips or any type of solid-state non-volatile semiconductor memory) on which information is permanently stored; and (ii) writable storage media (e.g., floppy disks within a diskette drive or hard-disk drive or any type of solid-state random-access semiconductor memory) on which alterable information is stored. Such computer readable storage media, when carrying computer-readable instructions that direct the functions of the methods described herein, are embodiments of the present disclosure. In some embodiments, the methods described herein, or portions thereof, are performed by one or more application specific integrated circuits (ASICs), field-programmable gate arrays (FPGAs), or other types of hardware implementations. In some other embodiments, the processes described herein are performed by a combination of software routines, ASIC(s), FPGAs and, or, other types of hardware implementations.

Operation of Reactor System

Figure 2:
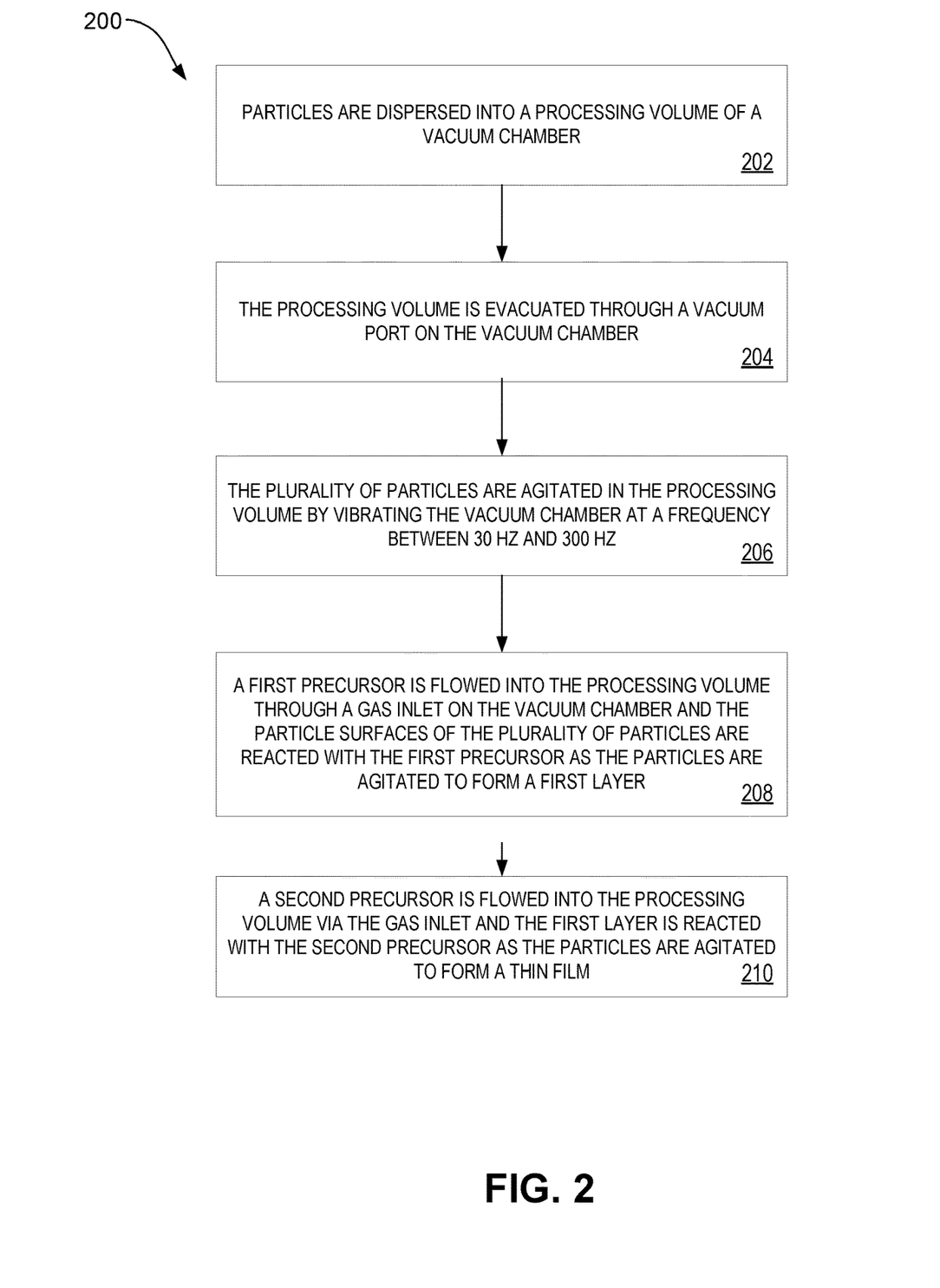
FIG. 2 is a flow diagram of an example process for utilizing the reactor system to coat particles.

FIG. 2 is a flow diagram of an example process 200 of utilizing the reactor system to coat particles. In a first step, particles are dispensed into a processing volume of a vacuum chamber (202). As described with reference to FIG. 1 reactor system 100 includes a vacuum chamber 101 having a lid 102 that can be used for loading/unloading of particles to be coated into the reactor system. A processing volume 107 defined by a first filter 105, a second filter 106, one or more sidewalls 103 of the vacuum chamber can receive the particles 120 loaded through the lid 102, e.g., by removing or adjusting the first filter 105 during the loading/unloading process.

In some implementations, the particles are loaded into the processing volume 107 using a porous processing vessel 111, where the porous processing vessel 111, e.g., a filter bag or container, is placed within the vacuum chamber 101 such that the particles 120 are located within the processing volume 107.

The particles (e.g., particles 120) can have a solid core comprising a drug, e.g., one of the drugs discussed above. The solid core can optionally also include an excipient. Once the lid 102 is sealed, a controller (e.g., controller 134) operates the reactor system (e.g., reactor systems 100) according to a recipe in order to form the thin-film metal oxide layers and/or thin polymer layers on the particles.

The processing volume is evacuated through a vacuum port on the vacuum chamber (204). The processing volume 107 can be evacuated through the vacuum port 114 located on the lid 102, where process gas within the processing volume 107 is evacuated through the filter 105. One or more vacuum sources 116 can be coupled through the vacuum port 114 by the exhaust manifold 118 to evacuate the processing volume 107 within the vacuum chamber 101. A low-pressure environment can be established within the volume 107 of the vacuum chamber 101, e.g., down to pressures below 1 Torr, e.g., to 1 to 500 mTorr, e.g., 50 mTorr.

The particles are agitated in the processing volume by vibrating the vacuum chamber at a frequency between 30 Hz and 300 Hz (206). The particles 120 are agitated within the processing volume 107 of the vacuum chamber 101. In some implementations, agitating the particles includes vibrating a table (e.g., table 142) coupled to the vacuum chamber 101 at a frequency between 30 Hz and 300 Hz, e.g., 30 Hz-150 Hz. Agitating the particles 120 using acoustic waves can be used to reduce particle agglomerations and disperse the particles 120 in the processing volume 107 so that the precursor gases can flow freely between the particles 120 and react with the surfaces of the particles 120.

In some implementations, a controller is configured to operate an oscillation driver 150 that is configured to induce vibrational motion in one or more vibrational actuators 148. The one or more vibrational actuators can be configured to generate a vibrational motion at a particular vibrational frequency in a table (e.g., table 142) supporting the vacuum chamber 101 such that particles 120 within the vacuum chamber 101 experience a vibrational frequency (e.g., ultrasonic frequency).

A first precursor gas is flowed into the processing volume through a gas inlet on the vacuum chamber and the particle surfaces of the particles are reacted with the first precursor as the particles are agitated to form a first layer (208). In some implementations, the first precursor gas can attach to the particle surfaces by physisorption. A mechanism of reaction can depend, for example, on the availability of functional groups on the surface of the particles. Physisorption can be a more likely mechanism, for example, in low temperature ALD/MLD processes. A first precursor gas 124a from the chemical distribution system 110 can be flowed into the processing volume 107 via gas inlet 108 located on the vacuum chamber 101. In some implementations, the gas inlet 108 is located on the vacuum chamber 101 such that process gas (e.g., the first precursor gas and the second precursor gas) flow into the processing volume through the second filter 106, into the processing volume 107, and is exhausted out of the processing volume 107 via the first filter 105 and out of the vacuum chamber 101 through vacuum port 114.

In some implementations, a first precursor is a metal, a metalloid, or a combination thereof, and a chemically functional group known as a ligand. For example, in some embodiments the first precursor comprises a moiety of Al, Ag, B, Ba, Be, Bi, Ca, Cd, Ce, Co, Cr, Cu, Dy, Eu, Er, Fe, Ga, Gd, Ge, Hf, Hg, Ho, In, Ir, La, Li, Lu, Mo, Mg, Mn, Nb, Nd, Ni, Os, Pd, Pr, Pt, Ru, Sb, Sc, Si, Sm, Sn, Sr, Ta, Ti, Tm, V, W, Y, Yb, Zn, Zr, or combinations thereof. In some embodiments, the chemically functional group is one of an alkyl, alkoxide, alkylamide, amidinate, carbonyl, cyclopentadienyl, β-diketonate, guandinate, or a halide.

In some implementations, the particle surfaces are reacted with the first precursor to form a first layer. The first layer can be a monolayer of an intermediate material including the reaction product of the first precursor and the particle surface. In some implementations, the reaction product includes a ligand of the first precursor.

A second precursor is flowed into the processing volume via the gas inlet and the first layer is reacted with the second precursor as the particles are agitated to form a thin film (210). In some implementations, the first layer is reacted with a second precursor to form a second layer. The second layer can be a monolayer including the reaction product of the first layer with the second precursor. In some implementations, the reaction product of the first layer with the second precursor is a ligand exchange reaction, e.g., a substitution reaction where the ligands of the first layer are substituted with a moiety of the second precursor. The ligands of the first layer can be released as volatile byproducts of the exchange reaction which are evacuated from the processing volume through an exhaust port (e.g., vacuum port 114) in fluid communication with the vacuum chamber 101.

In some implementations, repeated cycles of sequential exposure of the surfaces of the previously formed layers to the first and second precursors to form a material composition, e.g., a thin film coating of a desired thickness. In some implementations, the material composition of the thin film coating comprises a carbide, fluoride, nitride, oxide, phosphide, sulfide, or alloy composition of Al, B, Ba, Ca, Co, Cu, Fe, Ga, Ge, Hf, In, La, Mg, Nb, Ni, Pt, Ru, Sb, Si, Sr, Ta, Ti, V, W, Y, Zn, Zr, and combinations thereof. In other embodiments, such as in embodiments where one of the first or second layers is a sacrificial layer, the material composition of the thin film coating comprises a single element.

In some embodiments, the method includes purging the processing volume in a period between flowing of the first and the second precursor and between cycles of the first and second precursor. Typically, purging the processing volume includes one or more cycles of flowing a gas that is nonreactive with the deposition materials, such as $N_2$ or a noble gas, into the processing volume and evacuating the nonreactive gas from the vacuum chamber 101.

In some implementations, the reactor system performs an ALD and/or an MLD thin-film coating process by introducing gaseous precursors of the coating into the vacuum chamber 101. The gaseous precursors are spiked alternatively into the vacuum chamber 101. This permits the deposition process to be a solvent-free process. The half-reactions of the deposition process are self-limiting, which can provide Angstrom or nanometer level control of deposition. In addition, the ALD and/or MLD reaction can be performed at low temperature conditions, such as below 50° C., e.g., below 35° C. Flow rates of the process gas can be selected based on a type of process gas being injected. For example, a flow rate for a $H_2O$ process gas can be 1-2 standard liters per minute (slm) of vaporized precursor for 10 kg of powder. In another example, a flow rate for $H_2O$ process gas could range between 0.5-1 slm for powders with less surface area. In another example, TMA or $TiCl_4$ can have volumetric flow rates, for example, less than 1 slm. In another example, carrier gas flow rates can be, for example, in the 1-3 slm range for 10-15 kg of powder.

Suitable reactants for ALD methods include any of or a combination of the following: monomer vapor, metal-organics, metal halides, oxidants, such as ozone or water vapor, and polymer or nanoparticle aerosol (dry or wet). For example, the first fluid source 124a can provide gaseous trimethylaluminum (TMA) or titanium tetrachloride (TiCl4), whereas the second gas source 124b can provide water. For MLD methods, as an example, the fluid source 124c can provide adipoyl chloride, and the fourth fluid 124d can provide vaporous or gaseous ethylene diamine.

For both an ALD process and an MLD process, two reactant gases are alternately supplied to the vacuum chamber 101, with each step of supplying a reactant gas followed by a purge cycle in which the inert gas is supplied to the chamber 101 to force out the reactant gas and by-products used in the prior step.

In some implementations, the reactor system is operated in a continuous flow operation mode, e.g., for an ALD process. During an ALD process, the controller 134 can operate the reactor system 100 as follows. In a first reactant half-cycle, while the oscillation driver operates to generate a vibrational motion in the one or more vibrational actuators 148 to agitate the particles 120:

i) The chemical distribution system 110 is operated to flow the first reactant gas, e.g., TMA, from the source 124a into the vacuum chamber 101 via the gas inlet 108 until the particles 120 are saturated with the first reactant gas. For example, the first reactant gas can flow at a specified flow rate and for a specified period of time, or until a sensor measures a specified first pressure or partial pressure of the first reactant gas in the chamber 101. In some implementations, the first reactant gas is mixed with an inert gas as it flows into the chamber. The specified pressure or partial pressure can be 0.1 Torr to half of the saturation pressure of the reactant gas.

ii) Flow of the first reactant gas is halted, and the vacuum source 116 evacuates the chamber 101, e.g., down to pressures below 1 Torr, e.g., to 1 to 100 mTorr, e.g., 50 mTorr.

These steps (i)-(ii) can be repeated a number of times set by the recipe, e.g., two to ten times.

Next, in a first purge cycle, while the oscillation driver 150 operates to generate a vibrational motion in the one or more vibrational actuators 148 to agitate the particles 120:

iii) The chemical distribution system 110 is operated to flow only inert gas, e.g., N$_2$, from the source 124e into the chamber 101 via the gas inlet 108. The inert gas can flow at a specified flow rate and for a specified period of time, or until a sensor measures a specified second pressure of the inert gas in the chamber 101. The second specified pressure can be 1 to 100 Torr.

iv) The vacuum source 116 evacuates the chamber 101, e.g., down to pressures below 1 Torr, e.g., to 1 to 500 mTorr, e.g., 50 mTorr.

These steps (iii)-(iv) can be repeated a number of times set by the recipe, e.g., six to twenty times.

In a second reactant half-cycle, while the oscillation driver operates to generate a vibrational motion in the one or more vibrational actuators 148 to agitate the particles 120:

v) The chemical distribution system 110 is operated to flow the second reactant gas, e.g., H$_2$O, from the source 124b into the chamber 101 via the gas inlet 108 until the particles 120 are saturated with the second reactant gas. Again, the second reactant gas can flow at a specified flow rate and for a specified period of time, or until a sensor measures a specified third pressure or partial pressure of the second reactant gas in the chamber 101. In some implementations, the second reactant gas is mixed with an inert gas as it flows into the chamber. The third pressure can be 0.1 Torr to half of the saturation pressure of the second reactant gas.

vi) The vacuum source 116 evacuates the chamber 101, e.g., down to pressures below 1 Torr, e.g., to 1 to 500 mTorr, e.g., 50 mTorr.

These steps (v)-(vi) can be repeated a number of times set by the recipe, e.g., two to ten times.

Next, a second purge cycle is performed. This second purge cycle with steps (vii) and (viii) can be identical to the first purge cycle, or can have a different number of repetitions of the steps (iii)-(iv) and/or different specified pressure.

The cycle of the first reactant half-cycle, first purge cycle, second reactant half cycle and second purge cycle can be repeated a number of times set by the recipe, e.g., one to ten times.

The operation is discussed above with an ALD process, but the operation is similar for MLD. In particular, in steps (i) and (v), the reactant gasses are substituted with appropriate process gasses and pressures for deposition of a polymer layer. For example, step (i) can use vaporous or gaseous adipoyl chloride, and step (v) can use are vaporous ethylene diamine.

Moreover, although operation is discussed above with an ALD or MLD process, the system could be used for a chemical vapor deposition (CVD) process. In this case, both reactants are flowed simultaneously into the chamber 101 so as to react inside the chamber, e.g., during step (i). The second reactant half-cycle can be omitted.

In some implementations, the reactor system 100 is operated in a pulsed flow operation mode, where one or more of the gases (e.g., the reactant gases and/or the inert gas) can be supplied in pulses in which the chamber 101 is filled with the gas to a specified pressure, a delay time is permitted to pass, and the chamber is evacuated by the vacuum source 116 before the next pulse commences.

In particular, for an ALD process, the controller 134 can operate the reactor system 100 as follows.

In a first reactant half-cycle, while the oscillation driver operates to generate a vibrational motion in the one or more vibrational actuators 148 to agitate the particles 120:

i) The chemical distribution system 110 is operated to flow the first reactant gas, e.g., TMA, from the source 124a into the chamber 101 via the gas inlet 108 until a first specified pressure is achieved in the chamber 101. The specified pressure can be 0.1 Torr to half of the saturation pressure of the reactant gas.

ii) Flow of the first reactant gas is halted, and a specified delay time is permitted to pass, e.g., as measured by a timer in the controller. This permits the first reactant to flow through the particles 120 in the vacuum chamber 101 and react with the surface of the particles 120.

iii) The vacuum source 116 evacuates the chamber 101, e.g., down to pressures below 1 Torr, e.g., to 1 to 100 mTorr, e.g., 50 mTorr.

These steps (i)-(iii) can be repeated a number of times set by the recipe, e.g., two to ten times.

Next, in a first purge cycle, while the oscillation driver operates to generate a vibrational motion in the one or more vibrational actuators 148 to agitate the particles 120:

iv) The chemical distribution system 110 is operated to flow the inert gas, e.g., N$_2$, from the source 124e into the chamber 101 via the gas inlet 108 until a second specified pressure is achieved. The second specified pressure can be 1 to 100 Torr.

v) Flow of the inert gas is halted, and a specified delay time is permitted to pass, e.g., as measured by the timer in the controller. This permits the inert gas to diffuse through the particles 120 to displace the reactant gas and any vaporous by-products.

vi) The vacuum source 116 evacuates the chamber 101, e.g., down to pressures below 1 Torr, e.g., to 1 to 500 mTorr, e.g., 50 mTorr.

These steps (iv)-(vi) can be repeated a number of times set by the recipe, e.g., six to twenty times.

In a second reactant half-cycle, while the oscillation driver operates to generate a vibrational motion in the one or more vibrational actuators 148 to agitate the particles 120:

vii) The chemical distribution system 110 is operated to flow the second reactant gas, e.g., $H_2O$, from the source 124b into the chamber 101 via the gas inlet 108 until a third specified pressure is achieved. The third pressure can be 0.1 Torr to half of the saturation pressure of the reactant gas.

viii) Flow of the second reactant gas is halted, and a specified delay time is permitted to pass, e.g., as measured by the timer in the controller. This permits the second reactant gas to flow through the particles 120 and react with the surface of the particles inside the vacuum chamber 101.

ix) The vacuum source 116 evacuates the chamber 101, e.g., down to pressures below 1 Torr, e.g., to 1 to 500 mTorr, e.g., 50 mTorr.

These steps (vii)-(ix) can be repeated a number of times set by the recipe, e.g., two to ten times.

Next, a second purge cycle is performed. This second purge cycle can be identical to the first purge cycle, or can have a different number of repetitions of the steps (iv)-(vi) and/or different delay time and/or different pressure.

The cycle of the first reactant half-cycle, first purge cycle, second reactant half cycle and second purge cycle can be repeated a number of times set by the recipe, e.g., one to ten times.

Moreover, one or more of the gases (e.g., the reactant gases and/or the inert gas) can be supplied in pulses in which the vacuum chamber 101 is filled with the gas to a specified pressure, a delay time is permitted to pass, and the chamber is evacuated by the vacuum source 116 before the next pulse commences.

The operation is discussed above with an ALD process, but the operation is similar for MLD. In particular, in steps (i) and (vii), the reactant gasses are substituted with appropriate process gasses and pressures for deposition of a polymer layer. For example, step (i) can use vaporous or gaseous adipoyl chloride, and step (vii) can use are vaporous ethylene diamine.

Moreover, although operation is discussed above with an ALD or MLD process, the system could be used for a chemical vapor deposition (CVD) process. In this case, both reactants are flowed simultaneously into the chamber 101 so as to react inside the chamber, e.g., during step (i). The second reactant half-cycle can be omitted.

As noted above, the coating process can be performed at low processing temperature, e.g., below 50° C., e.g., at or below 35° C. In particular, the particles 120 can remain or be maintained at such temperatures during all of steps (i)-(ix) noted above. In general, the temperature of the interior of the reactor chamber does not exceed 35° C. during of steps (i)-(ix). This can be achieved by having the first reactant gas, second reactant gas and inert gas be injected into the chamber at such temperatures during the respective cycles. In addition, physical components of the chamber of the chamber can remain or be maintained at such temperatures, e.g., using a cooling system, e.g., a thermoelectric cooler, if necessary.

At the termination of the processing, e.g., at the end of the coating process, the particles 120 can be removed from the processing volume 107 via the lid 102, e.g., by removing or lifting the lid 102 off of the vacuum chamber 101. In some implementations, the particles 120 are located within the porous processing vessel 111 that is unloaded from the reactor system 100 by fully or partially removing the lid 102 from the vacuum chamber 101.

In some implementations, the controller 134 can cause the reactor system 100 to first deposit a metal oxide layer on the drug-containing particles, and then deposit a polymer layer over the metal oxide layer on the particles, e.g., using the process described above. In some implementations, the controller can cause the reactor system 100 alternate between depositing a metal oxide layer and depositing a polymer layer on the drug-containing particles, so as to form a multi-layer structure with layers of alternating composition.

The controller 134 and other computing devices part of systems described herein can be implemented in digital electronic circuitry, or in computer software, firmware, or hardware. For example, the controller can include a processor to execute a computer program as stored in a computer program product, e.g., in a non-transitory machine readable storage medium. Such a computer program (also known as a program, software, software application, or code) can be written in any form of programming language, including compiled or interpreted languages, and it can be deployed in any form, including as a standalone program or as a module, component, subroutine, or other unit suitable for use in a computing environment. In some implementations, the controller 134 is a general-purpose programmable computer. In some implementations, the controller can be implemented using special purpose logic circuitry, e.g., an FPGA (field programmable gate array) or an ASIC (application specific integrated circuit).

For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions. The present disclosure provides apparatus for and methods of preparing pharmaceutical compositions comprising API containing particles encapsulated by one or more layers of metal oxide and/or one or more layers of a polymer. The coating layers are conformal and of controlled thickness from several nanometers to several micrometers in total. The articles to be coated can be composed of only API or a combination of API and one or more excipients. The coating process described herein can provide an API with an increased glass transition temperature for the API relative to uncoated API, a decreased rate of crystallization for an amorphous form of the API relative to uncoated API, and decreased surface mobility of API molecules in the particle compared to uncoated API. Importantly, particle dissolution can be altered. Because the coating is relatively thin, drug products with high drug loading can be achieved. Finally, there are benefits with respect to cost and ease of manufacture because multiple coatings can be applied in the same reactor.

Terms of relative positioning are used to refer to relative positioning of components within the system or orientation of components during operation; it should be understood that the reactor system could be held in a vertical orientation or some other orientation during shipping, assembly, etc.

A number of embodiments of the invention have been described. Nevertheless, it will be understood that various modifications may be made without departing from the spirit and scope of the invention.

What is claimed is:

1. A method for coating particles, comprising:
    dispensing a plurality of particles into a processing volume of a vacuum chamber, wherein the processing volume is defined by one or more sidewalls of the vacuum chamber, a first filter, and a second filter;
    evacuating the processing volume through a vacuum port on the vacuum chamber;
    agitating the plurality of particles disposed in the processing volume of the vacuum chamber by vibrating the vacuum chamber at a frequency between 30 Hz and 300 Hz;
    flowing a first precursor into the processing volume through a gas inlet on the vacuum chamber and through the first filter and reacting particle surfaces of the plurality of particles with the first precursor as the particles are agitated to form a first layer; and
    flowing a second precursor into the processing volume via the gas inlet and reacting the first layer with the second precursor as the particles are agitated to form a thin film,
    wherein the plurality of particles are retained within the processing volume while the first and second precursors are flowed.

2. The method of claim 1, wherein dispensing particles into the processing volume of the vacuum chamber further comprises placing a porous processing vessel enclosing the plurality of particles into the processing volume.

3. The method of claim 2, wherein the porous processing vessel comprises the first filter and the second filter.

4. The method of claim 1, wherein the plurality of particles have a dimension less than about 300 micron.

5. The method of claim 1, wherein the vacuum chamber is located on and supported by a vibrational table.

6. The method of claim 1, further comprising flowing a purge gas into the processing volume between flowing the first precursor and flowing the second precursor.

7. The method of claim 6, further comprising a plurality of repeated cycles of flowing the first precursor into the processing volume, flowing the purge gas into the processing volume, and flowing the second precursor into the processing volume.

8. The method of claim 1, comprising coating the particles by atomic layer deposition or molecular layer deposition.

9. The method of claim 1, further comprising exhausting the first precursor from the processing volume through the vacuum port on the vacuum chamber.

10. The method of claim 9, further comprising exhausting the second precursor from the processing volume through the vacuum port on the vacuum chamber.

11. The method of claim 1, wherein flowing the first precursor and flowing the second precursor comprises:
    forcing the first precursor and the second precursor through the first filter located below and supportive of the plurality of particles and wherein the first precursor and the second precursor are exhausted through the second filter located above the plurality of particles within the processing volume, and
    wherein the first precursor and the second precursor percolate through the plurality of particles within the processing volume.

12. The method of claim 1, wherein agitating the plurality of particles disposed in the processing volume comprises inducing separation of particles of the plurality of particles such that the first precursor and the second precursor flows between particles of the plurality of particles.

13. The method of claim 1, wherein vibrating the vacuum chamber comprises alternating between vibrations being perpendicular and parallel to gravity.

* * * * *